United States Patent [19]
Costantini et al.

[11] Patent Number: 5,354,919
[45] Date of Patent: Oct. 11, 1994

[54] OXIDATION OF AROMATIC COMPOUNDS SUBSTITUTED BY OXIDIZABLE ALKYL MOIETIES

[75] Inventors: Michel Costantini; Dominique Laucher, both of Lyons; Eric Fache, Villeurbanne, all of France

[73] Assignee: Rhone-Poulenc Chimie, Courbevoie Cedex, France

[21] Appl. No.: 84,028

[22] Filed: Jun. 29, 1993

[30] Foreign Application Priority Data

Jun. 29, 1992 [FR] France .................. 92 07950
Mar. 26, 1993 [FR] France .................. 93 03488

[51] Int. Cl.$^5$ ........................................... C07C 45/32
[52] U.S. Cl. ............................... 568/432; 568/426; 568/431
[58] Field of Search .................. 568/426, 431, 432

[56] References Cited

U.S. PATENT DOCUMENTS

| | | | |
|---|---|---|---|
| 3,714,263 | 1/1973 | Cyba | 568/432 |
| 4,453,016 | 6/1984 | Au et al. | 568/432 |
| 4,471,140 | 9/1984 | Au | 568/432 |
| 4,748,278 | 5/1988 | Röhrscheid | 568/438 |
| 4,915,875 | 4/1990 | Diephouse et al. | 568/432 |

Primary Examiner—Werren B. Lone
Attorney, Agent, or Firm—Burns, Doane, Swecker & Mathis

[57] ABSTRACT

Aromatic compounds bearing oxidizable alkyl substituents, e.g., alkoxylated and/or hydroxylated such substrates, notably the phenolics/cresols, are selectively oxidized, e.g., into hydroxybenzaldehydes, by reacting same with appropriate oxidizing agents, in an aqueous reaction medium, in the presence of a catalytically effective amount of a solid, palladium-containing oxidation catalyst (optionally containing a cocatalytically effective amount of tin, germanium, tellurium and/or copper).

32 Claims, No Drawings

OXIDATION OF AROMATIC COMPOUNDS SUBSTITUTED BY OXIDIZABLE ALKYL MOIETIES

BACKGROUND OF THE INVENTION

1. Field of the Invention

The present invention relates to the oxidation of aromatic compounds bearing an oxidizable alkyl group, notably for the preparation of aromatic ketones or aldehydes.

This invention especially relates to the oxidation of aromatic compounds bearing an oxidizable alkyl group and a hydroxyl and/or alkoxy group, notably for the preparation of hydroxy and/or alkoxy-aromatic ketones or aldehydes.

In a preferred embodiment of the present invention, cresols are oxidized into corresponding hydroxybenzaldehydes.

2. Description of the Prior Art

EP-A-12,939, U.S. Pat. No. 4,453,016 and U.S. Pat. No. 4,471,140 describe the oxidization of p-cresol by means of molecular oxygen in the presence of sodium or potassium hydroxide and a catalyst, such as a compound of cobalt, nickel or chromium, to produce the alkali metal salts of p-hydroxybenzaldehyde.

A preferred embodiment entails using methanol as the reaction solvent and cobalt salts as the catalyst.

Such processes employ a large excess of potassium or sodium hydroxide, providing highly concentrated and viscous reaction media. Moreover, in order to separate the p-hydroxybenzaldehyde formed, it is necessary to neutralize the excess of base, which promotes the formation of large amounts of salts.

To obviate these disadvantages, U.S. Pat. No. 4,748,278 describes a process to isolate the p-hydroxybenzaldehyde formed, but this entails supplementary stages.

Moreover, JP-A-63/154,644 describes a process for the oxidation of p-cresol by means of oxygen, in the presence of a catalyst formed from cobalt acetate, cobalt bromide and manganese acetate. The reaction is conducted in a mixture of acetic acid and acetic anhydride, because it is necessary to protect the hydroxyl group by transforming it into an acetoxy group.

Therefore, such process suffers from the disadvantage of requiring the protection of the hydroxyl group. Too, the reaction is not aldehyde selective, because more acid forms, the yield of the acetoxybenzoic acid obtained being approximately 80%.

SUMMARY OF THE INVENTION

Accordingly, a major object of the present invention is the provision of an improved process for the oxidation of aromatic substrates, notably phenolic compounds, inter alia cresols, which is carried out in a single stage, requires no protection of the hydroxyl group, and prepares, e.g., aldehydes, with good selectivity and in good reaction yields.

Another object of this invention is the provision of an improved process for the oxidation of O-alkylated phenolic compounds substituted by an oxidizable alkyl group.

Briefly, the present invention features a process for the oxidation of an aromatic compound substituted by an oxidizable alkyl group and having the general formula (I):

in which Y is an oxidizable alkyl group; n is a number ranging from 1 to 5 and preferably equal to 1, 2 or 3; R is a hydrocarbon radical having from 1 to 24 carbon atoms selected from among a straight or branched, saturated aliphatic radical, a monocyclic or polycyclic, saturated, unsaturated or aromatic cycloaliphatic radical, or a straight or branched, saturated aliphatic radical bearing a cyclic substituent, with the proviso that two R substituents borne by two oxygen atoms depending from adjacent carbon atoms of the aromatic nucleus may together form, with the oxygen atoms from which they depend, a saturated, unsaturated or aromatic heterocycle having 5 to 8 atoms, said oxidation reaction being carried out in water or in a mixture of water and an organic solvent, in the presence of a catalytically effective amount of a solid catalyst comprising an active phase deposited onto a support and including palladium, optionally associated with another metallic element selected from among tin, germanium, tellurium and copper.

DETAILED DESCRIPTION OF PREFERRED EMBODIMENTS OF THE INVENTION

More particularly according to the present invention, by the term "aromatic compound substituted by an oxidizable alkyl group" is intended an aromatic compound bearing at least one oxidizable alkyl substituent.

By the term "aromatic compound" is intended the standard concept of aromaticity such as is defined in the literature, particularly by Jerry March, *Advanced organic Chemistry*, Third Edition, John Wiley & Sons, p. 37 ff(1985).

By the term "oxidizable alkyl group" is intended an alkyl group, whose carbon atom directly bonded to the carbon atom of the aromatic nucleus bears at least two free hydrogen atoms.

The aromatic substrate which is oxidized under the conditions according to the invention, for example, is an aromatic compound substituted by an oxidizable alkyl group and an alkoxy and/or hydroxyl group. By the term "alkoxy" is generically intended all O-alkylation radicals symbolized by the formula —O—R, in which R is as defined above. Thus, the radical R represents a hydrogen atom or a hydrocarbon radical having 1 to 24 carbon atoms and preferably an "alkyl" radical.

The radical R can be of a random nature provided that it remains inert under the reaction conditions. As it is an aliphatic radical, it can be interrupted by a heteroatom (e.g., oxygen), or by a functional group (e.g., CO), or can bear a substituent (e.g., a halogen). As it can be a cyclic radical, preferably cyclohexyl or phenyl, the latter can also be substituted. Any random substituent can be present on such cycle to the extent that it does not interfere with the desired product. The substituents can, inter alia, be the radicals $R_4$ defined below:

Particularly advantageous aromatic substrates that are oxidized according to the process of the invention include those of the general formula (I'):

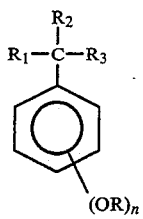

(I')

in which n is a number equal to 1, 2 or 3; $R_1$ and $R_2$ are each a hydrogen atom; $R_3$ is a hydrogen atom, an alkyl radical having from 1 to 12 carbon atoms, an optionally substituted phenyl radical of the formula:

in which $R_4$ is a hydrogen atom, an alkyl radical having from 1 to 12 carbon atoms, an alkoxy radical having from 1 to 10 carbon atoms or a hydroxyl group and m is a number equal to 0, 1, 2 or 3, an alkoxy radical having from 1 to 10 carbon atoms, a halogen atom, a radical $R_5$—CO—X—, in which $R_5$ is a straight or branched alkyl radical having from 1 to 10 carbon atoms, a phenyl radical, a $CF_3$—radical, an alkoxy radical having from 1 to 10 carbon atoms or a phenoxy group and X is a valence bond or an oxygen atom; and the radicals R, which may be identical or different, are each a hydrogen atom, an alkyl radical having from 1 to 12 and preferably 1 to 6 carbon atoms, or an optionally substituted phenyl radical, with the proviso that two R substituents borne by two oxygen atoms depending from adjacent carbon atoms of the aromatic nucleus may together form, with the oxygen atoms from which they depend, a saturated, unsaturated or aromatic heterocycle having 5 to 8 atoms.

By the term "halogen atom" is intended a chlorine, bromine or fluorine atom.

When n is equal to or greater than 1, the R substituents borne by the two oxygen atoms depending from adjacent carbon atoms of the aromatic nucleus can be linked together to form a cycle via an alkylene radical having 1 to 4 carbon atoms, thus forming a ketal bridge, such as methylene dioxy or ethylene dioxy radicals.

The present invention is more particularly applicable to aromatic compounds having the formula (I), in which R is a hydrogen atom or a straight or branched alkyl radical having from 1 to 4 carbon atoms.

The process according to the invention is even more particularly applicable to phenolic compounds substituted by an oxidizable group, having the general formula (I) or (I'), in which R is a hydrogen atom.

Preferred substrates according to the invention include phenol substrates, notably o-cresol, p-cresol, m-cresol, 4-ethylphenol, (2-methoxymethyl)phenol, 1,2-dihydroxy-4-methylbenzene and 4,4'-dihydroxydiphenyl methane.

The process of the invention is well suited for the oxidization of cresols and, more particularly, for oxidizing p-cresol into p-hydroxybenzaldehyde and m-cresol into m-hydroxybenzaldehyde.

Exemplary O-alkylated aromatic substrates of formula (I) includes o-methylanisole, p-methylanisole, m-methylanisole, 3,4-dioxymethylene toluene, p-phenoxytoluene and p-4-hydroxyphenoxytoluene.

The invention is also well suited for the oxidation of p-methylanisole and 3,4-dioxymethylene toluene.

The process of the invention can be carried out in a solvent, which can be water or a mixture of water and an organic solvent. The solvent must be inert under the reaction conditions. In the following description, by the term "reaction solvent" is intended water or a mixture of water and an organic solvent. The water can be water alone, or an acid, neutral or slightly basic aqueous solution.

An aqueous solution of a mineral acid, or an acid salt, such as boric acid, sulfuric acid, potassium acetate, potassium carbonate, sodium hydrogen sulfate, potassium hydrogen sulfate can thus be used; similarly useful is an aqueous solution of a neutral salt, e.g., potassium nitrate, potassium sulfate or magnesium sulfate, an aqueous solution of a mineral base or a basic salt, such as sodium hydroxide, potassium hydroxide, ammonium hydroxide, or basic potassium carbonate.

The concentration of the aqueous solution in acid, base or salt advantageously ranges from $10^{-3}$ to 1 mole/liter.

According to the process of the invention, water can be used as the reaction solvent. In this event, in the absence of an organic solvent, an acid, neutral or slightly basic aqueous solution as defined above is preferably employed. A mixture of water and organic solvent is also suitable for conducting the process of the invention. By the term "organic solvent" is intended a protic or aprotic, polar or apolar, organic solvent.

Exemplary protic polar organic solvents suitable for the invention include, inter alia, carboxylic acids or their precursors and alcohols or polyols.

The carboxylic acids which can be used can be monocarboxylic or polycarboxylic. These are compounds devoid of unsaturation. Particularly preferred are those having the following general formula (II):

$$R'—COOH \qquad (II)$$

in which R' is a hydrocarbon radical having from 1 to 24 carbon atoms, which can be a straight or branched, saturated, acyclic, aliphatic radical, a monocyclic or polycyclic, saturated or aromatic, cycloaliphatic radical.

The radical R' can be substituted by another COOH functional group. It can also bear other substituents, e.g., alkoxy or halogen, provided that they do not interfere with the reaction. R' more particularly is a straight or branched, alkyl radical having from 1 to 4 carbon atoms, a cycloalkyl radical having from 5 to 7 carbon atoms, or a phenyl radical.

Exemplary such carboxylic acids which can be used in the process of the invention are aliphatic monocarboxylic acids, e.g., acetic, propionic, butyric, valeric or hexanoic acid; aliphatic dicarboxylic acids, e.g., malonic, succinic or adipic acid; cycloaliphatic acids, e.g., cyclopentane carboxylic or cyclohexane carboxylic acid; benzoic, naphthoic or phenylacetic acid.

Among the aforementioned carboxylic acids, acetic and propionic acids are the preferred.

Exemplary protic, polar, organic solvents suitable for the present invention include the monohydroxylated or polyhydroxylated alcohols. Particularly advantageous are alcohols having the general formula (III):

$$R''-OH \qquad (III)$$

in which R'' is a hydrocarbon radical having from 1 to 24 carbon atoms, which can be a straight or branched, saturated, acyclic, aliphatic radical, or a monocyclic, saturated, cycloaliphatic radical.

The radical R'' can be substituted by another OH functional group. It can also bear other substituents, e.g., alkoxy or halogen, provided that they do not interfere with the reaction. R'' is preferably a straight or branched alkyl radical having from 1 to 4 carbon atoms, or a cycloalkyl radical having from 5 to 7 carbon atoms.

Exemplary monohydroxylated or polyhydroxylated alcohols suitable for the process of the invention include the aliphatic monoalcohols such as methanol, ethanol, propanol, butanol, sec.-butanol, tert. butanol, pentanol, hexanol; aliphatic dialcohols such as ethylene glycol, diethylene glycol or propylene glycol; and cycloaliphatic alcohols such as cyclopentanol or cyclohexanol. Among the above alcohols, the preferred alcohols are methanol, ethanol and tert. butanol.

Aprotic, polar, organic solvents are also suitable for carrying out the process of the invention, particularly nitro compounds such as nitromethane, nitroethane, 1-nitropropane, 2-nitropropane or mixtures thereof and nitrobenzene; aliphatic or aromatic nitriles such as acetonitrile, propionitrile, butane nitrile, isobutane nitrile, benzonitrile and benzyl cyanide; and tetramethylene sulfone (sulfoiane). Among the above solvents, acetonitrile is particularly preferred.

It is also possible to use slightly polar aprotic solvents such as aliphatic, cycloaliphatic or aromatic etheroxides and, more particularly, diethyl oxide, dipropyl oxide, diisopropyl oxide, dibutyl oxide, methyl tert. butyl ether, dipentyl oxide, diisopentyl oxide, ethylene glycol dimethyl ether (or 1,2-dimethoxyethane), diethylene glycol dimethyl ether (or 1,5-dimethoxy-3-oxapenetane), dioxane or tetrahydrofuran; phosphoric neutral esters such as, in particular, trimethyl phosphate, triethyl phosphate, tributyl phosphate, triisobutyl phosphate or tripentyl phosphate; ethylene carbonate; aliphatic or aromatic, halogenated hydrocarbons and, more particularly, perchlorinated hydrocarbons, specifically carbon tetrachloride, tetrachloroethylene and hexachloroethylene; partially chlorinated hydrocarbons such as dichloromethane, chloroform, 1,2-dichloroethane, 1,1,1-trichloroethane, 1,1,2,2-tetrachloroethane, pentachloroethane, trichloroethylene, 1-chlorobutane, 1,2-dichlorobutane; monochlorobenzene, 1,2-dichlorobenzene, 1,3-dichlorobenzene, 1,4-dichlorobenzene, 1,2,4-trichlorobenzene, or mixtures of different chlorobenzenes; bromoform, bromoethane or 1,2-dibromoethane; monobromobenzene or mixtures of monobromobenzene and one or more dibromobenzene; 1-bromonaphthalene. Dioxane is the preferred.

Another class of solvents which are suitable are nonpolar, aprotic solvents such as aliphatic or aromatic hydrocarbons and, more particularly, hexane, heptane, octane, nonane, decane or cyclohexane, benzene and naphthalene.

According to the process of the invention, the oxidation of the aromatic substrate can be carried out in a mixture of water and organic solvent. The amount of water in the water/organic solvent mixture can vary widely. Thus, the weight ratio between the water and the organic solvent advantageously ranges from 0.05 to 0.95 and preferably from 0.20 to 0.80.

One of the features of the process according to the invention is that water is always present in the reaction mixture.

The molar ratio of the water to the aromatic substrate to be oxidized advantageously ranges from 20 to 1,000 and preferably is approximately 100.

The concentration of the aromatic substrate to be oxidized in the reaction solvent can also vary over wide limits. Thus, it advantageously ranges from 0.01 to 5 moles of aromatic substrate per liter of reaction solvent and preferably from 0.05 to 1.0 mole/liter.

Also according to the invention, a solid catalyst is employed, which comprises at least the metallic element palladium, which can be associated with other metallic elements selected from among tin, germanium, tellurium and copper. It is also possible to use bimetallic or trimetallic catalysts.

Exemplary catalysts suitable for the invention are those incorporating the following elements: palladium, palladium/tin, palladium/germanium, palladium/copper, palladium/tellurium, palladium/tellurium/copper and palladium/tin/copper.

Particularly advantageous are catalysts based on palladium/tin and palladium/germanium.

The above metallic elements are deposited onto a support, whose nature can vary widely. Particularly suitable such supports include active charcoals, silica gels, silica-alumina mixtures, alumina, clays, bauxite, magnesia and diatomaceous earth.

For good performance, the preferred supports are charcoals, which are generally activated by a known treatment carried out using nitric acid.

The active catalytic phase comprising palladium, to which has optionally been added another metallic element such as referred to above, generally represents at most 20% by weight of the solid catalyst, although higher contents can indeed be used. With regard to the minimum amount, the active phase constitutes at least 0.1% of the weight of the solid catalyst. The amount of active catalytic phase comprising the catalyst can vary widely and preferably constitutes from 0.5 to 10% of the solid catalyst weight.

When the catalyst has additional metallic elements, the amount thereof is such that the molar ratio between the palladium and the other metallic elements preferably ranges from 0.01 to 10 and more preferably from 0.1 to 5.0.

The amount of catalyst to be used compared with the aromatic substrate to be oxidized can also vary over wide limits. Thus, the amount of catalyst expressed by the molar ratio between the metallic element or elements and the aromatic compound substituted by an oxidizable alkyl group can range from 0.01 to 0,001 and preferably from 0.05 to 0.01.

To prepare the supported catalyst according to the invention, conventional procedures can be employed which are known per se for the preparation of supported metallic catalysts. In respect of such preparation of the various catalysts, see, in particular, J. F. Lepage, "Catalyse de contact, conception, preparation et mise en oeuvre des catalyseurs industriels", Edition Technip, (1978).

The catalyst can, e.g., be prepared by introducing a support into a solution formulated by dissolving at least one appropriate compound of the selected element or elements. The active element or elements are deposited onto the support by distilling the solvent and the thus obtained contact mass is subjected to a reduction by means of a stream of hydrogen gas, or by a reducing compound such as hydrazine, methanol or formaldehyde.

In another conventional preparative technique, the deposition of the compound or compounds providing the active elements onto the support is carried out by precipitating the compounds in per se known manner and subjecting the thus obtained hydrazine mass to a reduction, more particularly by hydrogen, hydrazine, methanol or formaldehyde.

Other preparative techniques are also possible, in particular the impregnation of a support by means of a solution of the appropriate compound or compounds in the presence of an organic reducing agent as indicated above. The deposition onto the support of a plurality of metallic elements can obviously be carried out simultaneously or successively.

It is generally preferable to use a prereduced catalyst, i.e., first subjected to a reduction as defined above. The reduction of the catalyst is carried out hot, typically at a temperature ranging from 200° C. to 250° C. This is particularly advantageous in the event that catalysts are used containing only palladium.

The nature of the compounds providing the metallic elements used for the preparation of the catalysts according to the invention is not critical. The actual metals can also be used, such as palladium, tin, germanium, tellurium and copper.

Exemplary compounds which can be used for the preparation of the catalysts of the invention are hydrated or unhydrated palladium oxide, palladium dioxide, palladium nitrate or palladium acetate. As regards the additional metallic elements, the oxides, nitrates, carboxylates and alkoxides of tin, germanium, tellurium or copper can be used, or organometallic compounds in which the aforesaid metals are bonded to a hydrogen atom and/or alkyl radicals preferably having from 1 to 4 carbon atoms. The preferred salts are compounds of tin (II), such as tin (II) acetate, tin (II) octoate, tin ethyl hexanote; tellurium monoxide or trioxide; germanium oxide, germanium ethylate, tetrabutyl germanium; cuprous oxide, cupric oxide, cupric sulfate, cupric acetate or cupric methylate.

The size of the catalyst particles advantageously ranges from 0.1 to 1.0 mm; it will be appreciated that larger or smaller sizes can also be used. The size of these particles is dependent on the operating procedure selected.

As indicated above, the aromatic compounds substituted by an oxidizable alkyl group are oxidized in the reaction solvent in the presence of the solid catalyst and an oxidizing agent. The reaction is advantageously carried out in the liquid phase, suspending the solid catalyst in the reaction medium incorporating the aromatic compound substituted by an oxidizable alkyl group, the reaction solvent and an oxidizing agent.

Particularly exemplary oxidizing agents which can be used in the process of the invention include hydrogen peroxide, peracetic acid, tert. butyl hydroperoxide and cyclohexyl hydroperoxide. The hydrogen peroxide is advantageously used in its commercial form, namely, an aqueous solution having a concentration of approximately 70%.

The amount of oxidizing agent introduced can vary over wide limits. It is typically the stoichiometric amount, or even in slight excess of up to 20% more than the stoichiometric amount.

The preferred oxidizing agents are molecular oxygen or gases comprised thereof. Such a gas can be pure oxygen or oxygen diluted with an inert gas, e.g., nitrogen or a rare gas, preferably argon. Air can thus be used.

The amount of oxygen used is not critical, provided that neither the supply gases, nor any gaseous phase likely to appear in the reaction zone are within the range of explosive compositions, taking account of the reaction conditions or other parameters. The amount of oxygen can either be in excess or deficient in respect of the stoichiometry of the reaction, vis-a-vis the substrate to be oxidized. The reaction pressure advantageously ranges from atmospheric pressure to approximately 200 bar. A pressure ranging from 1 to 100 bar is preferred.

The process according to the invention can be carried out under atmospheric pressure, permitting pure oxygen to bubble through the reaction medium at a flow rate of, e.g., 1 to 50 liters/hour.

In another embodiment of the invention, the process is conducted under pressure in an autoclave. In this event, diluted oxygen is used, preferably air, under a pressure advantageously ranging from 80 to 100 bar. The reaction temperature advantageously ranges from 40° to 190°, and preferably from 50° to 120° C.

From a practical standpoint, the following materials are introduced into the reactor in random order, the reaction solvent, the solid catalyst and the aromatic substrate to be oxidized. In the event that the oxidizing agent is in the liquid state, it is introduced at the same time as the other reagents.

The reaction medium is stirred and heated to the reaction temperature selected. When the oxidizing agent is in gaseous state, molecular oxygen or a gas comprised thereof is then supplied. At the end of the reaction, the solid catalyst is separated by conventional solid/liquid separation techniques, preferably by filtration or by decanting. The oxidized compound obtained, aldehyde or ketone, is recovered by any appropriate means, e.g., by distillation of the reaction solvent.

As indicated above, the process according to the invention is more particularly applicable to the oxidation of cresols, preferably p-cresol to hydroxybenzaldehydes.

It is also within the scope of the invention to carry out the subject process by oxidizing an aromatic compound substrate substituted by an oxidizable group and having the formula (I), in which the benzene nucleus is replaced by a naphthene or other such nucleus.

In order to further illustrate the present invention and the advantages thereof, the following specific examples are given, it being understood that same are intended only as illustrative and in nowise limitative.

In Examples 1 to 23, the apparatus used was identical. It comprised a 100 ml, glass spherical flask, provided with an effective central stirring system, a condenser, as well as an oxygen supply via a dropper, with heating being provided by an oil bath.

In said examples, the abbreviations have the following definitions:

$$\text{Conversion rate} = \frac{\text{number of moles of converted aromatic substrate}}{\text{number of moles of aromatic substrate introduced}}$$

$$\text{Selectivity} = \frac{\text{number of moles of aldehyde formed}}{\text{number of moles of aromatic substrate converted}}$$

The percentages given in the examples are by weight.

EXAMPLE 1

(a) Treatment of carbon black employed as the catalyst support

Activated carbon black marketed by CECA S.A. of type 3S and having a BET surface of 1,150 m$^2$/g (100 g) was suspended in an aqueous, 30% nitric acid solution (600 ml). The mixture was refluxed for 2 hours. The aqueous solution was removed by filtration and the carbon black was washed with demineralized water until the pH of the wash water was 4. The carbon black was dried at 90° C. under a reduced pressure of 20 mm of mercury.

(b) Preparation of a catalyst containing palladium and germanium

Into a 300 ml autoclave were introduced carbon black (10 g), treated as above, suspended in toluene (150 ml), followed by tetrabutyl germanium (6.02 g, 20 mmole) and palladium acetate (1.08 g, 4.42 mmole). Heating was conducted at 80° C. for 2 hours with effective stirring under 20 kg/cm$^2$ of hydrogen. The autoclave was cooled, the catalyst recovered by filtration under argon and dried under a reduced pressure of 20 mm of mercury.

(c) Oxidation of p-cresol

The thus prepared catalyst (1 g) was reacted in accordance with the following operating procedure. Into the reactor were introduced 10 ml of acetic acid, 0 ml of water, 0.98 g (10 mmole) of potassium acetate, 1.1 g (10 mmole) of p-cresol and 1 g of palladium/germanium catalyst on carbon.

In this and all other examples, the acetic acid used was 99% acetic acid.

The reaction mixture was then stirred, heated at 100° C. for 2 hours and oxygen introduced therein at a rate of 5 liters/hour. The reactor was cooled and its content determined by high performance liquid chromatography (HPLC). The p-cresol conversion was 50%.

0.8 mmole of p-(hydroxymethyl)phenol, 2.2 mmole of p-hydroxybenzaldehyde and 0.3 mmole of p-hydroxybenzoic acid were obtained.

EXAMPLE 2

This example illustrates the use of palladium deposited onto carbon black as the catalyst.

The catalyst was prepared by precipitating palladium from palladium chloride in accordance with the known technique described in J. F. Lepage, "Catalyse de contact, conception, preparation et mise en oeuvre des catalyseurs industriels," Edition Technip (1978).

Into the reactor were introduced 10 ml of acetic acid, 40 ml of water, 0.98 g (10 mmole) of potassium acetate, 1.1 g (10 mmole) of p-cresol and 1 g of catalyst, namely, palladium on carbon black (3S) incorporating 5% by weight palladium.

This was followed by stirring, heating at 100° C. for 2 hours and the introduction of oxygen at a rate of 5 liters/hour. The reactor was cooled and its content determined by high performance liquid chromatography (HPLC). The p-cresol conversion was 60%.

0.18 m/hole of p-(acetoxymethyl)phenol, 1.11 mmole of p-hydroxybenzaldehyde and 0.2 mmole of p-hydroxybenzoic acid were obtained.

EXAMPLE 3

(a) Preparation of a catalyst containing palladium and tin

Into a spherical flask, as described hereinbefore, were introduced 400 ml of acetic acid, 2.44 g (10 mmole) of palladium acetate Pd (OAc)$_2$, 9.8 g (100 mmole) of potassium acetate and 20 g of caron black treated in accordance with the operating procedure described in Example 1.

Stirring was carried out for 15 minutes at ambient temperature, followed by the addition of 16.1 g (40 mmole) of tin (II) ethyl hexanoate. Heating was then carried out for 4 hours at 110° C., accompanied by stirring.

The spherical flask was cooled, the catalyst collected by filtration under argon, washed twice with 50 ml acetic acid and dried at 50° C. under 20 mm of mercury. The catalyst contained 4.3% by weight of palladium and 2% by weight tin.

(b) Oxidation of p-cresol

The thus prepared catalyst (1.0 g) was reacted in accordance with the operating procedure of Example 2. The p-cresol conversion was 96%.

0.3 mmole of p-(hydroxymethyl)phenol, 5.2 mmole of p-hydroxybenzaldehyde and 1 mmole of p-hydroxybenzoic acid were obtained.

EXAMPLE 4

The catalyst (0.5 g) prepared in Example 3 was reacted in accordance with the operating procedure of Example 2, except that the reaction was conducted in a mixture of 30 ml of acetic acid and 20 ml of water. The reaction temperature was 100° C. The p-cresol conversion was 87%.

0.9 mmole of p-(acetoxymethyl)phenol, 5.6 mmole of p-hydroxybenzaldehyde and 0.75 mmole of p-hydroxybenzoic acid were obtained.

EXAMPLE 5

The catalyst (0.5 g) prepared as in Example 3 was reacted according to the operating procedure of Example 2, except that the reaction was conducted in a mixture of 20 ml of methanol and 30 ml of an aqueous sulfuric acid solution at pH=1. The reaction temperature was 80° C. The p-cresol conversion was 80%.

5.4 mmole of p-hydroxybenzaldehyde and 0.7 mmole of methyl p-hydroxybenzoate were obtained.

EXAMPLE 6

The catalyst (1 g) prepared in Example 3 was reacted according to the operating procedure of Example 2, except that the acetic acid was replaced by tert. butanol and the reaction temperature was 80° C. The p-cresol conversion was 50%. 2.2 mmole of p-hydroxybenzaldehyde and 0.2 mmole of p-hydroxybenzoic acid were obtained.

EXAMPLE 7

This example employed a palladium/copper/tin catalyst prepared from a palladium/copper catalyst on carbon marketed by Engelhard containing 53% by weight palladium, 1.5% by weight copper and 53% by weight water.

2 g of a palladium/copper on carbon catalyst, 20 ml of acetic acid, 30 ml of water, 1.02 g (9.4 mmole) of p-cresol and 0.9 g (2.25 mmole) of tin (II) ethyl hexanoate were introduced into the reactor. Heating was carried out for 2 hours at 100° C., accompanied by stirring, and while introducing oxygen at a rate of 5 liters/hour. The p-cresol conversion was 70%.

2.9 mmole of p-hydroxybenzaldehyde and 0.8 mmole of p-hydroxybenzoic acid were obtained.

EXAMPLE 8

(a) Preparation of a catalyst containing palladium, tellurium and copper

Into a 30% nitric acid aqueous solution were dissolved 1.63 g (7.3 mmole) of palladium acetate Pd(OAc)$_2$, 0.105 g (0.66 mmole) of tellurium dioxide TeO$_2$, and 4 g (20 mmole) of copper acetate Cu(OAc)$_2$·H$_2$O.

Carbon black (15 g) treated according to Example 1 was suspended in this solution. The solvent was evaporated under reduced pressure and the thus obtained solids were dried at 80° C. under a reduced pressure of 20 mm of mercury. The catalyst was reduced for 2 hours at 200° C. and 2 hours at 400° C. by a methanol-saturated nitrogen stream (60 liters hour). It was then treated for 15 hours at 300° C. with nitrogen (60 liters/hour) containing 2% oxygen and was again reduced for 2 hours at 200° C. and 2 hours at 400° C. with a methanol-saturated nitrogen stream.

(b) Oxidation of p-cresol

A test was carried out using the thus prepared catalyst (1 g). Into the reactor were introduced 1 g of catalyst, 20 ml of acetic acid, 30 ml of water and 1.22 g (11.3 mmole) of p-cresol. This was followed by heating for 2 hours at 100° C., accompanied by stirring, and while introducing oxygen at a rate of 5 liters/hour. The p-cresol conversion was 50%.

2.9 mmole of p-hydroxybenzaldehyde and 0.3 mmole of p-hydroxybenzoic acid were obtained.

EXAMPLE 9

The catalyst (0.5 g) prepared in Example 3 was reacted in accordance with the operating procedure of Example 2, except that the reaction was conducted in a mixture of 25 ml of water and 25 ml of dioxane. The reaction temperature was 90° C. The p-cresol conversion was 60%.

1.2 mmole of p-(hydroxymethyl)phenol and 3.3 mmole of p-hydroxybenzaldehyde were obtained.

EXAMPLE 10

The reaction was carried out in a two-phase medium in this example.

The catalyst (0.5 g) prepared in Example 3 was reacted according to the operating procedure of Example 2, except that the reaction was conducted in a mixture of 25 ml of chlorobenzene, 12.5 ml of acetic acid and 12.5 ml of water. The p-cresol conversion was 35%.

1.6 mmole of p-(hydroxymethyl)phenol and 1.0 mmole of p-hydroxybenzaldehyde were obtained.

EXAMPLE 11

The reaction was carried out in this example using hydrogen peroxide as the oxidizing agent.

The catalyst (1.0 g) prepared in Example 3 was introduced into the reactor, together with 25 ml of water, 25 ml of acetic acid, 25 mmole of hydrogen peroxide, 10 mmole of p-cresol and 10 mmole of potassium acetate. Stirring and heating were carried out for 2 hours at 100° C. The hydrogen peroxide conversion was 100% and the p-cresol conversion 84%.

3.0 mmole of p-hydroxybenzaldehyde and 2.7 mmole of p-hydroxybenzoic acid were obtained.

EXAMPLE 12

In this example, the reaction was conducted under pressure.

The catalyst (0.5 g) prepared in Example 3 was introduced into a 150 ml autoclave together with 25 ml of water, 25 ml of acetic acid, 10 mmole of p-cresol and 10 mmole of potassium acetate.

The autoclave was placed under a pressure of 40 bar of air containing, by volume, 20% oxygen and 80% nitrogen and heated at 130° C. for 2 hours. The autoclave was cooled and depressurized to atmospheric pressure. The p-cresol conversion was 100%.

6.8 mmole of p-hydroxybenzaldehyde and 1 mmole of p-hydroxybenzoic acid were obtained.

EXAMPLE 13

The catalyst used was the catalyst containing palladium and tin of Example 3.

Into the reactor were introduced 25 ml of acetic acid, 25 ml of water, 0.98 g (10 mmole) of potassium acetate, 1.1 g (10 mmole) of p-cresol and 1 g of catalyst. This was followed by stirring and heating at 100° C. for 2 hours, while admitting oxygen at a rate of 5 liters/hour. The reactor was cooled and its content determined by high performance liquid chromatography (HPLC). The p-cresol conversion was 79%.

0.84 mmole of p-(acetoxymethyl)phenol, 0.28 mmole of p-(hydroxymethyl)phenol, 4.82 mmole of p-hydroxybenzaldehyde and 0.59 mmole of p-hydroxybenzoic acid were obtained.

EXAMPLE 14

This example used as the catalyst palladium deposited onto carbon black.

The catalyst was obtained by precipitating palladium from palladium chloride according to the procedure described by J. F. Lepage, supra.

Into the reactor were introduced 25 ml of acetic acid, 25 ml of water, 0.98 g (10 mmole) of potassium acetate, 1.1 g (10 mmole) of p-cresol and 0.5 g of catalyst, namely, palladium on carbon black (3S) incorporating 3% by weight palladium. This was followed by stirring, heating at 100° C. for 4 hours and introducing oxygen at a rate of 5 liters/hour. The reactor was cooled and its content determined by high performance liquid chromatography (HPLC). The p-cresol conversion was 11%.

0.26 mmole of p-(acetoxymethyl)phenol, 0.37 mmole of p-(hydroxymethyl)phenol, 0.21 mmole of p-hydroxybenzaldehyde and 0.2 mmole of p-hydroxybenzoic acid were obtained.

EXAMPLE 15

The catalyst of Example 14 was used in this example.

After treatment at 200° C. under a 1 liter/hour hydrogen stream, the catalyst was reacted according to the operating procedure of Example 14, except that the reaction time was 2 hours instead of 4. The p-cresol conversion was 40%.

1.2 mmole of p-(acetoxymethyl)phenol, 1.0 mmole of p-(hydroxymethyl)phenol, 2.1 mmole of p-hydroxybenzaldehyde and 0.2 mmole of p-hydroxybenzoic acid were obtained.

EXAMPLE 16 filtrate and the wash waters were determined by HPLC and the catalyst was used for a fresh oxidation reaction.

The results obtained are reported in the following Table:

TABLE

| Example | Recycled number | Conversion rate | p-(hydroxy-methyl)phenol (mmole) | p-(acetoxy-methyl)phenol (mmole) | p-hydroxy-benzaldehyde (mmole) | p-hydroxy-benzoic acid (mmole) |
| --- | --- | --- | --- | --- | --- | --- |
| 19(a) | 0 | 56.2 | 0.82 | 1.25 | 2.84 | 0.31 |
| 19(b) | 1 | 63.7 | 0.78 | 1.03 | 3.66 | 0.31 |
| 19(c) | 2 | 65.8 | 0.55 | 0.79 | 4.97 | 0.38 |
| 19(d) | 3 | 75.8 | 0.20 | 0.58 | 5.21 | 0.81 |

This example used the catalyst and the operating procedure of Example 14, except that the reaction time was 4 hours, 30 minutes. The p-cresol conversion was 87%.

1.8 mmole of p-(acetoxymethyl)phenol, 6.0 mmole of p-hydroxybenzaldehyde and 0.7 mmole of p-hydroxybenzoic acid were obtained.

EXAMPLE 17

This example used the catalyst and operating procedure of Example 14, except that the reaction time was 21 hours. The p-cresol conversion was 100%.

6.9 mmole of p-hydroxybenzaldehyde and 3.0 mmole of p-hydroxybenzoic acid were obtained.

EXAMPLE 18

This example used as the catalyst palladium deposited onto silica, SPHEROSIL X400LS ®.

The palladium was deposited onto the support in accordance with the conventional exchange procedure using, as the palladium precursor, the compound Pd(NH$_3$)$_4$(OH)$_2$. The catalyst was prereduced in the manner described in Example 15 and then 25 ml of acetic acid, 25 ml of water, 0.98 (10 mmole) of potassium acetate, 1.1 g (10 mmole) of p-cresol and 0.5 g of catalyst, namely, palladium on silica, SPHEROSIL X400LS, incorporating 3% by weight palladium, were charged into the reactor.

This was followed by stirring, heating at 100° C. for 2 hours and introducing oxygen at a rate of 5 liters/hour. The reactor was cooled and its content determined by high performance liquid chromatography (HPLC). The p-cresol conversion was 38%.

0.6 mmole of p-(acetoxymethyl)phenol, 0.5 mmole of p-(hydroxymethyl)phenol, 2.3 mmole of p-hydroxybenzaldehyde and 0.2 mmole of p-hydroxybenzoic acid were obtained.

EXAMPLES 19(a) TO 19(d)

This example employed, as the catalyst, palladium on carbon black.

In a first test, a novel catalyst was used and, in the following tests, a recycled catalyst was employed. The catalyst was prereduced in the manner descried in Example 15, followed by the introduction, into the reactor, of 25 ml of acetic acid, 25 ml of water, 0.98 g (10 mmole) of potassium acetate, 1.1 g (10 mmole) of p-cresol and 0.5 g of catalyst, namely, palladium on carbon black (3S) incorporating 3% by weight palladium.

This was followed by stirring, heating at 100° C. for 2 hours and introducing oxygen at a rate of 5 liters/hour. The reactor was cooled and the reaction medium filtered. The catalyst was washed with acetic acid. The

Comparative Example A

The catalyst used was that containing palladium and tin of Example 3.

The procedure of Example 13 was repeated, except that the reaction medium did not contain water. 50 ml of acetic acid were used. Stirring was carried out with heating at 100° C. for 2 hours and oxygen was introduced at a rate of 5 liters/hour. The reactor was cooled and its content determined by HPLC. The p-cresol conversion was 100%.

5.2 mmole of p-(acetoxymethyl)phenol, 2.4 mmole of p-hydroxybenzaldehyde and 1.2 mmole of p-hydroxybenzoic acid were obtained.

EXAMPLE 20

(a) Preparation of a catalyst containing palladium deposited onto carbon black

This catalyst was prepared by precipitating palladium from palladium chloride according to the procedure described by J. F. Lepage, supra. The palladium content in the catalyst was 3%. The catalyst was reduced at 200° C. under a hydrogen stream (1 liter/hour) for 2 hours.

(b) Oxidation of 4-methylanisole

Into a 300 ml reactor were introduced 25 ml of acetic acid, 25 ml of water, 0.98 g (10 mmole) of potassium acetate, 1.2 g (10 mmole) of 4-methylanisole, and 1 g of catalyst in the form palladium/carbon black.

This was followed by stirring, heating at 100° C. for 4 hours and introducing oxygen at a rate of 5 liters/hour. The reactor was cooled and its content determined by high performance liquid chromatography (HPLC). The 4-methylanisole conversion was 60%.

0.16 mmole of p-(hydroxymethyl)anisole, 2.6 mmole of p-(acetoxymethyl)anisole, 1.9 mmole of p-methoxybenzaldehyde and 0.4 mmole of p-methoxybenzoic acid were obtained.

EXAMPLE 21

The procedure of Example 20 was repeated except that the 4-methylanisole was replaced by 2-methylanisole. The 2-methylanisole conversion was 50%.

0.2 mmole of o-(hydroxymethyl)anisole, 2.7 mmole of o-(acetoxymethyl)anisole, 0.52 mmole of o-methoxybenzaldehyde and 0.06 mmole of o-methoxybenzoic acid were obtained.

EXAMPLE 22

The procedure of Example 20 was repeated, except that the 4-methylanisole was replaced by 3- methylanisole. The 3-methylanisole conversion was 30%.

0.12 mmole of m-(hydroxymethyl)anisole, 0.63 mmole of m-(acetoxymethyl)anisole, 0.31 mmole of m-methoxybenzaldehyde and 0.09 mole of m-methoxybenzoic acid were obtained.

EXAMPLE 23

This example employed methylene-3,4-dioxytoluene.

The catalyst used was the catalyst containing palladium and tin of Example 3.

Into the reactor were introduced 40 ml of acetic acid, 10 ml of water, 0.98 g (10 mmole) of potassium acetate, 1.36 g (10 mmole) of methylene-3,4-dioxytoluene and 1 g of catalyst in the form palladium/tin.

This was followed by stirring, heating at 100° C. for 4 hours and introducing oxygen at a rate of 5 liters/hour. The reactor was cooled and its content determined by HPLC. The methylene-3,4-dioxytoluene conversion was 20%.

0.2 mmole of (methylene-3,4-dioxy)benzyl acetate, 0.4 mmole of methylene, 3,4-dioxybenzaldehyde and 0.68 mmole of (methylene-3,4--dioxy)-benzoic acid were obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the oxidation of an aromatic compound substituted by an oxidizable alkyl substituent, comprising reacting said aromatic compound substituted by an oxidizable alkyl substituent with an oxidizing agent, in an aqueous reaction medium, in the presence of a catalytically effective amount of a solid, palladium-containing oxidation catalyst so as to produce an oxidized aromatic product, wherein the oxidizable alkyl substituent is bonded to the aromatic compound by way of a carbon atom which has at least two free hydrogen atoms.

2. The process as defined by claim 1, said aromatic compound substituted by an oxidizable alkyl substituent is further substituted by at least one alkoxy or hydroxyl substituent.

3. The process as defined by claim 1, said solid oxidation catalyst comprising a catalytically active palladium phase deposited onto a support substrate therefor.

4. The process as defined by claim 3, said active catalyst phase further comprising a cocatalytically effective amount of tin, germanium, tellurium, copper, or admixture thereof.

5. The process as defined by claim 1, said aqueous reaction medium comprising water or an aqueous solution.

6. The process as defined by claim 1, said aqueous reaction medium comprising a water/organic solvent admixture.

7. The process as defined by claim 1, said aromatic compound substituting by an oxidizable alkyl substituent having the general formula (I):

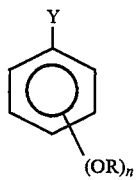

in which Y is an oxidizable alkyl radical; n is a number ranging from 1 to 5; and R is a hydrogen atom or a hydrocarbon radical having from 1 to 24 carbon atoms selected from among a straight or branched, saturated aliphatic radical, a monocyclic or polycyclic, saturated, unsaturated or aromatic cycloaliphatic radical, or a straight or branched, saturated aliphatic radical bearing a cyclic substituent, with the proviso that two R groups depending from two oxygen atoms borne by adjacent carbon atoms of the aromatic nucleus may together form, with the oxygen atoms from which they depend, a saturated, unsaturated or aromatic heterocycle having 5 to 8 atoms.

8. The process as defined by claim 7, said aromatic compound substituted by an oxidizable alkyl substituent having the general formula (I'):

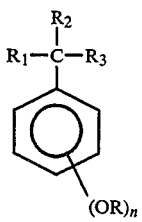

in which n is a number equal to 1, 2 or 3; $R_1$ and $R_2$ are each a hydrogen atom; $R_3$ is a hydrogen atom, an alkyl radical having from 1 to 12 carbon atoms, an optionally substituted phenyl radical of the formula:

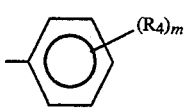

in which $R_4$ is a hydrogen atom, an alkyl radical having from 1 to 12 carbon atoms, an alkoxy radical having from 1 to 10 carbon atoms or a hydroxyl group, and m is a number equal to 0, 1, 2 or 3, an alkoxy radical having from 1 to 10 carbon atoms, a halogen atom, a radical $R_5$—CO—X—, wherein $R_5$ is a straight or branched alkyl radical having from 1 to 10 carbon atoms, a phenyl radical, a $CF_3$—radical, an alkoxy radical having from 1 to 10 carbon, or a phenoxy radical, and X is a valence bond or an oxygen atom; and the radicals R, which may be identical or different, are each a hydrogen atom, an alkyl radical having from 1 to 12 carbon atoms, or an optionally substituted phenyl radical, with the proviso that two R groups depending from two oxygen atoms borne by adjacent carbon atoms of the aromatic nucleus may together form, with the oxygen atoms from which they depend, a saturated, unsaturated or aromatic heterocycle having 5 to 8 atoms.

9. The process as defined by claim 7, wherein said aromatic compound having the general formula (I), R is a hydrogen atom or an alkyl radical having from 1 to 4 carbon atoms.

10. The process as defined by claim 1, said aromatic compound comprising o-cresol, p-cresol, m-cresol, 4-ethylphenol, (2-methoxymethyl)phenol, 1,2-dihydroxy-4-methylbenzene or 4,4'-dihydroxy diphenyl methane.

11. The process as defined by claim 10, said aromatic compound comprising p-cresol or m-cresol.

12. The process as defined by claim 1, said aromatic compound comprising o-methylanisole, p-methylanisole, m-methylanisole, 3,4-dioxymethylenetoluene, p-phenoxytoluene or p-4-hydroxyphenoxytoluene.

13. The process as defined by claim 12, said aromatic compound comprising p-methylanisole or 3,4-dioxymethylenetoluene.

14. The process as defined by claim 1, said aqueous reaction medium comprising water or an acid, neutral or slightly basic aqueous solution.

15. The process as defined by claim 14, said aqueous reaction medium comprising an aqueous solution of a mineral acid or an acid salt, an aqueous solution of a neutral salt, or an aqueous solution of a mineral base or a basic salt.

16. The process as defined by claim 6, said aqueous reaction medium comprising a protic or aprotic, polar or apolar, organic solvent.

17. The process as defined by claim 6, said aqueous reaction medium comprising acetic or propionic acid, methanol, ethanol, tert. butanol, acetonitrile or dioxane.

18. The process as defined by claim 6, wherein the weight ratio between the water and the organic solvent in said aqueous reaction medium ranges from 0.05 to 0.95.

19. The process as defined by claim 1, wherein the molar ratio of the water in said aqueous reaction medium to said aromatic compound ranges from 20 to 1,000.

20. The process as defined by claim 1, wherein the concentration of said aromatic compound in said aqueous reaction medium ranges from 0.01 to 5 moles of aromatic compound per liter of reaction medium.

21. The process as defined by claim 1, the catalytically active phase of said solid catalyst comprising palladium, palladium/tin, palladium/germanium, palladium/copper, palladium/tellurium, palladium/tellurium/copper, or palladium/tin/copper.

22. The process as defined by claim 21, the catalytically active phase of said solid catalyst comprising palladium/tin or palladium/germanium.

23. The process as defined by claim 3, said catalyst support substrate comprising active charcoal, silica gel, silica-alumina, alumina, clay, bauxite, magnesia or diatomaceous earth.

24. The process as defined by claim 1, said solid catalyst being prereduced.

25. The process as defined by claim 1, the catalytically active phase of said solid catalyst comprising from 0.1 to 20% by weight thereof.

26. The process as defined by claim 1, said oxidizing agent comprising hydrogen peroxide, or molecular oxygen or a gas containing molecular oxygen.

27. The process as defined by claim 1, carried out under a reaction pressure ranging from atmospheric pressure to approximately 200 bar.

28. The process as defined by claim 27, carried out at a temperature ranging from 40° to 190° C.

29. The process as defined by claim 7 wherein said oxidation catalyst comprises a catalytically active palladium phase deposited onto support substrate therefor.

30. The process as defined by claim 29, said active catalyst phase further comprising a cocatalytically effective amount of tin, germanium, tellurium, copper or admixtures thereof.

31. The process as defined by claim 29, said aqueous reaction medium comprising water or an aqueous solution.

32. The process as defined by claim 29, said aqueous reaction medium comprising water/organic solvent admixture.

* * * * *